United States Patent
Chen et al.

(10) Patent No.: US 11,001,671 B2
(45) Date of Patent: May 11, 2021

(54) DIAMINE-DIACID SALT, COPOLYMER AND METHOD FOR MANUFACTURING THE SAME

(71) Applicant: INDUSTRIAL TECHNOLOGY RESEARCH INSTITUTE, Hsinchu (TW)

(72) Inventors: Yu-Ting Chen, Tianzhong Township (TW); Jiun-Jy Chen, Toufen Township (TW); Tun-Fun Way, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 125 days.

(21) Appl. No.: 16/190,782

(22) Filed: Nov. 14, 2018

(65) Prior Publication Data

US 2019/0144605 A1 May 16, 2019

Related U.S. Application Data

(60) Provisional application No. 62/586,402, filed on Nov. 15, 2017.

(30) Foreign Application Priority Data

Oct. 4, 2018 (TW) ................... 107135079

(51) Int. Cl.
| | | |
|---|---|---|
| *C08G 69/28* | (2006.01) | |
| *C07C 231/02* | (2006.01) | |
| *C07C 237/34* | (2006.01) | |
| *C07C 233/78* | (2006.01) | |

(52) U.S. Cl.
CPC ............ *C08G 69/28* (2013.01); *C07C 231/02* (2013.01); *C07C 233/78* (2013.01); *C07C 237/34* (2013.01)

(58) Field of Classification Search
None
See application file for complete search history.

(56) References Cited

U.S. PATENT DOCUMENTS

| 5,399,306 A | 3/1995 | Follows et al. |
| 2005/0234215 A1 | 10/2005 | Gaymans et al. |
| 2006/0293487 A1* | 12/2006 | Gaymans ........... C08G 18/4854 528/44 |
| 2016/0130397 A1* | 5/2016 | Clauss .................. C08G 69/28 528/339 |
| 2016/0168381 A1 | 6/2016 | Washio et al. |

FOREIGN PATENT DOCUMENTS

| CN | 103881087 A | 6/2014 |
| CN | 104558593 A | 4/2015 |
| CN | 104387581 B | 8/2016 |
| CN | 104558594 B | 10/2017 |
| EP | 3 118 241 A1 | 1/2017 |
| JP | 2013-1770 A | 1/2013 |

(Continued)

OTHER PUBLICATIONS

Schuur et al (Synthesis and characterization of bisester-amide segments of uniform and random length, Polymer 46 (2005) 4584-4595). (Year: 2005).*

*Primary Examiner* — Rachel Kahn
(74) *Attorney, Agent, or Firm* — Birch, Stewart, Kolasch & Birch, LLP

(57) ABSTRACT

A method of forming a copolymer is provided, which includes (i) mixing a diamine and a diester to form a mixture, and heating the mixture to form a diamine compound, wherein the diamine compound has a chemical structure of

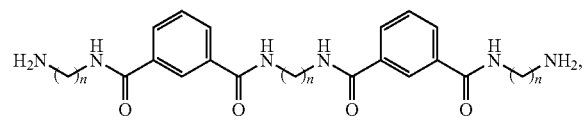

(ii) mixing the diamine compound and a diacid to form a diamine-diacid salt, wherein the diamine-diacid salt has a chemical structure of

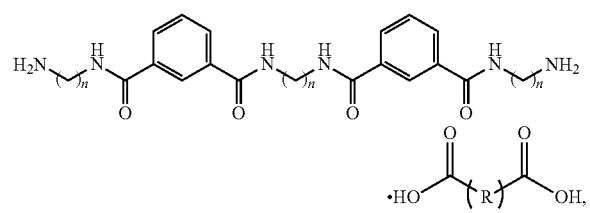

and (iii) heating the diamine-diacid salt to polymerize the diamine-diacid salt for forming a copolymer, wherein the copolymer has a repeating unit with a chemical structure of

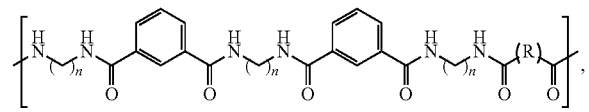

wherein n=2-12, R is

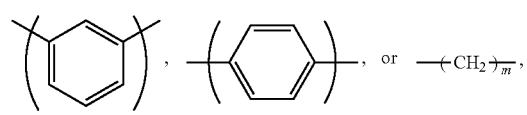

and m=2-12.

5 Claims, No Drawings

(56) References Cited

FOREIGN PATENT DOCUMENTS

| JP | 2013-1836 A | 1/2013 |
| JP | 2014-240135 A | 12/2014 |
| JP | 2014-240138 A | 12/2014 |
| JP | 2015-124260 A | 12/2014 |
| TW | 201718703 A | 6/2017 |

\* cited by examiner

DIAMINE-DIACID SALT, COPOLYMER AND METHOD FOR MANUFACTURING THE SAME

CROSS REFERENCE TO RELATED APPLICATIONS

This application claims the benefit of U.S. Provisional Application No. 62/586,402, filed on Nov. 15, 2017, and Taiwan Application Serial Number 107135079, filed on Oct. 4, 2018, the entirety of which are hereby incorporated by reference herein.

TECHNICAL FIELD

The technical field relates a diamine compound.

BACKGROUND

Transparent polyamide (nylon) is currently used in applications like packaging materials and overlay materials for optical instruments. The major commercially available nylons are polymerized of three or more monomers. Although these nylons achieve the purpose of being transparent, three or more monomers are necessary. Different monomers differ greatly in how they react, so the sequence of the repeating units in the nylon products is difficult to control. As such, the molecular sequence distribution is random, variations in physical properties are high, and stability is low in nylon products. In addition, some commercially available nylons are aliphatic polymer, which have disadvantages such as poor thermal resistance, high water absorption (resulting in processing being difficult and oxygen permeability being too high), low Tg about 40° C. to 60° C.), and poor mechanical strength. A nylon product polymerized of aromatic monomer such as isophthalate (IPA), e.g. representative transparent product PA-6I/6T/66 (6I/6T<30%, and I content <20%), may overcome the disadvantages of the aliphatic transparent polymer. However, the water absorption (6.8%/8.0%, percent equilibrium water at 23° C. and 100% RH) of PA-6I/6T/66 needs to be improved further. If water absorption is reduced to less than 5.8 the I content (e.g. IPA content) should be increased. However, a conventional nylon product with an I content higher than 25% is very brittle and difficult to process.

SUMMARY

One embodiment of the disclosure provides a diamine compound having a chemical structure of

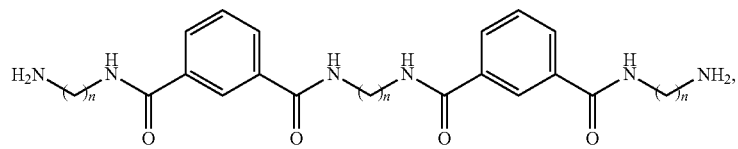

wherein n=2-12.

One embodiment of the disclosure provides a diamine-diacid salt having a chemical structure of

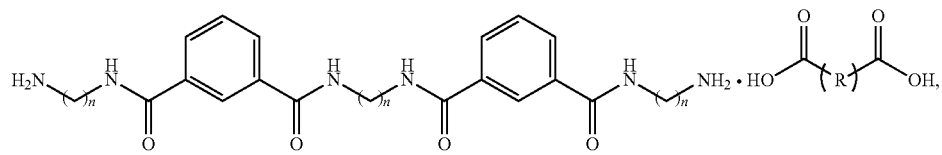

wherein n=2-12, R is

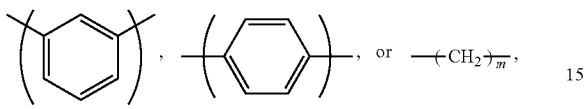

and m=2-12.

One embodiment of the disclosure provides a copolymer having a repeating unit with a chemical structure of

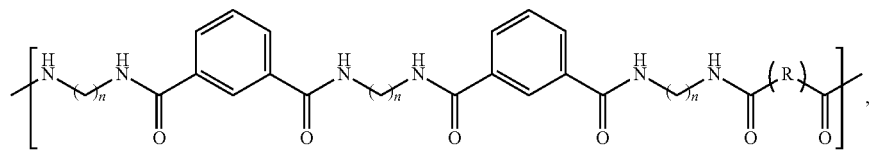

wherein n=2-12, R is

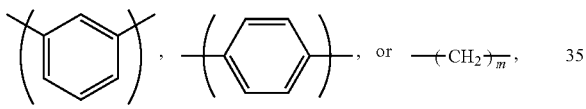

and m=2-12.

One embodiment of the disclosure provides a method of forming a diamine compound, including: (i) mixing diamine and diester to form a mixture, and heating the mixture to form a diamine compound, wherein the diamine compound has a chemical structure of

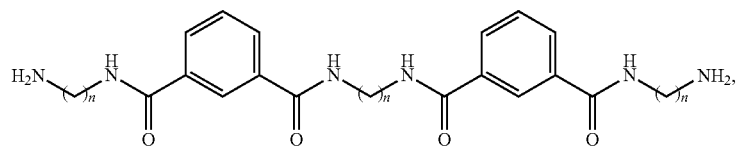

wherein n=2-12.

One embodiment of the disclosure provides a method of forming a copolymer, including: (i) mixing a diamine and a diester to form a mixture, and heating the mixture to form a diamine compound, wherein the diamine compound has a chemical structure of

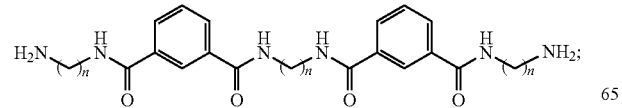

(ii) mixing the diamine compound and a diacid to form a diamine-diacid salt, wherein the diamine-diacid salt has a chemical structure of

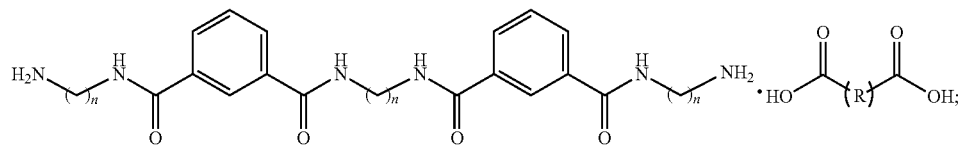

and (iii) heating the diamine-diacid salt to polymerize the diamine-diacid salt for forming a copolymer, wherein the copolymer has a repeating unit with a chemical structure of

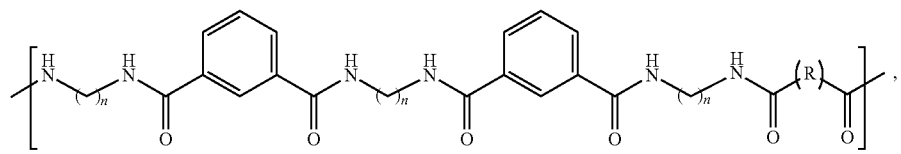

wherein n=2-12, R is

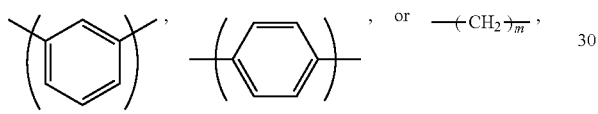

and m=2-12.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

One embodiment of the disclosure provides a method of forming a diamine compound, including: (i) mixing diamine and diester to form a mixture, and heating the mixture to form a diamine compound. The reaction is shown below:

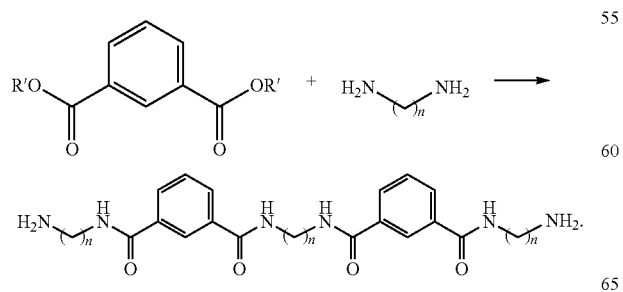

In the above formula, n=2-12, depending on the type of the diamine. In one embodiment, the diamine can be hexamethylenediamine (n=6), another suitable diamine, or a combination thereof. In one embodiment, n=4-8. In the above formula, R' depends on the type of diester. For example, the diester includes bis(hydroxyethyl)isophthalate, dimethyl isophthalate, another suitable isophthalate, or a combination thereof. In one embodiment, R' can be $C_{1-6}$ alkyl group.

In one embodiment, the mixture is heated to a temperature of 70° C. to 100° C. If the mixture is heated by a temperature that is too low, this results in the reactivity being poor and the reaction being incomplete, so that only one ester group of the diester reacts with diamines and another ester group of the diester maintains or hydrolyzes to acid. Moreover, the reaction needs a very long period. If the mixture is heated by a temperature that is too high, this results in degradation of the product. In one embodiment, the diamine and the diester have a molar ratio of 6:1 to 11:1. A diamine ratio that is too low results in a poor reactivity and incomplete reaction, in which only one ester group of the diester reacts with diamines and another ester group of the diester either maintains unreacted or hydrolyzes to acid. When the diamine ratio is too high, it is difficult to purify the product.

One embodiment of the disclosure also provides a method of forming a diamine-diacid salt, including (ii) mixing the diamine compound and a diacid to form a diamine-diacid salt. The reaction is shown below:

and m=4 or 8. In one embodiment, R is

and m=4-8. Alternatively, the diacid can be terephthalic acid or isophthalic acid, in which R is

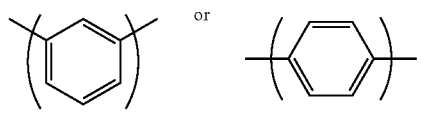

The diamine compound and the diacid are mixed to form the diamine-diacid salt at a temperature of room temperature (about 25° C.) to 80° C. If the diamine compound and the diacid are mixed at a temperature that is too low, the reaction will be incomplete and the reaction period will take longer. If the diamine compound and the diacid are mixed at a temperature that is too high, a side product may occur. In one embodiment, the diamine compound and the diacid have a molar ratio of 1:1.6 to 1:3.0. If the diacid ratio is too low, not

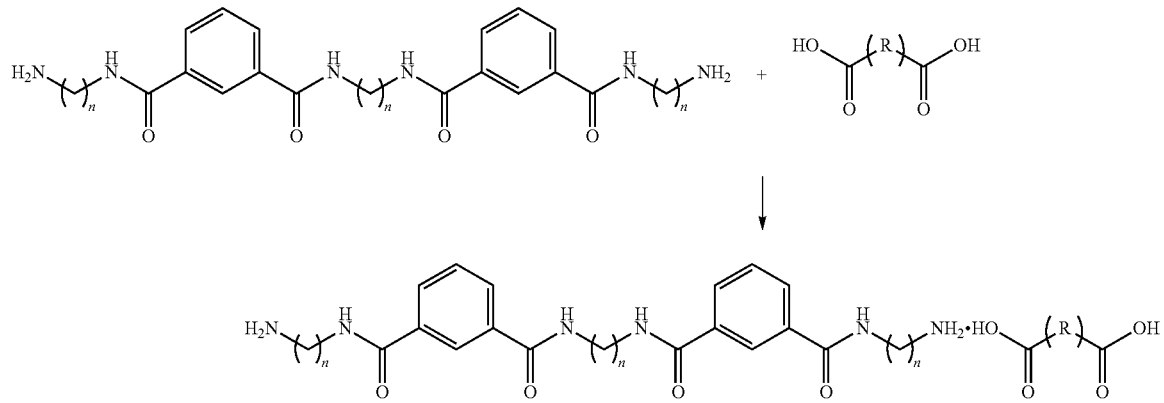

In the above formula, n=2-12, R is

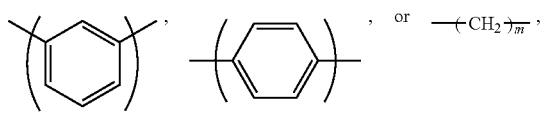

and m=2-12. R depends on the type of the diacid. For example, the diacid can be adipic acid or sebacic acid, in which R is

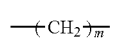

all of the diamine compound will react to form the diamine-diacid salt, and not all of the salt will have a 1:1 ratio of diamine compound to diacid. If the diacid ratio is too high, it will be difficult to purify the salt product.

One embodiment of the disclosure also provides a method of forming a copolymer, including heating the diamine-diacid salt to polymerize the diamine-diacid salt to form a copolymer, wherein the copolymer has a repeating unit with a chemical structure of

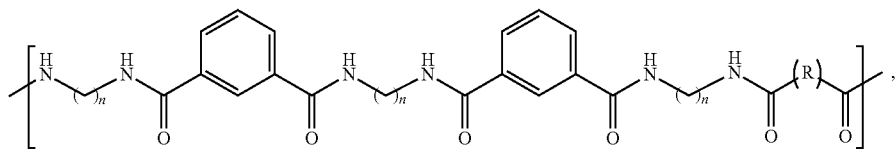

wherein n=2-12, R is

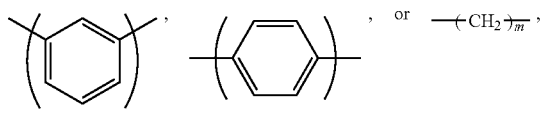

and m=2-12. In one embodiment, the step of heating the diamine-diacid salt to form the copolymer is performed at a temperature of 200° C. to 260° C. If the polymerization temperature of the diamine-diacid salt is too low, a partial crystallized copolymer may form. If the diamine-diacid salt is heated at a temperature that is too high, amine exchange or even degradation may occur, thereby forming a random copolymer rather than an alternating copolymer. The copolymer formed by the above steps is amorphous alternating copolymer. In one embodiment, the copolymer has a relative viscosity of 2.0 to 3.5. A copolymer having a relative viscosity that is too low has a molecular weight that is too low, and it thereby has poor thermal resistance and mechanical properties. A copolymer having a relative viscosity that is too high may be difficult to process and be too brittle. The copolymer can be further laminated to form a sheet. The sheet will simultaneously have excellent film formability, high transparency, low water absorption, high glass transfer temperature (Tg), and high tensile strength, and the like.

Note that steps (i), (ii), and (iii) are possible steps but not the only steps to form the diamine compound, the diamine-diacid salt, and the copolymer. One skilled in the art may select any other reasonable synthesis steps to form the diamine compound, the diamine-diacid salt, and the copolymer, which are not limited to the above steps and the corresponding reactants.

On the other hand, the diamine compound not only forms the diamine-diacid salt with the diacid, but also reacts with another compound to form a product that is not limited to the diamine-diacid salt. Similarly, the diamine-diacid salt is not only heated to form the copolymer, but also polymerized with another monomer to form another copolymer.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

Synthesis of Diamine Compound 15.2 g of bis(hydroxyethyl)isophthalate (BHEI, 0.06 mole), 70 g of hexamethylenediamine (HMDA, 0.6 mole), and 0.85 g of sodium acetate were added to a round bottom bottle (250 mL), and then heated to 90° C. and stirred for 24 hours. The result of the reaction was cooled down to room temperature. The reaction is shown below:

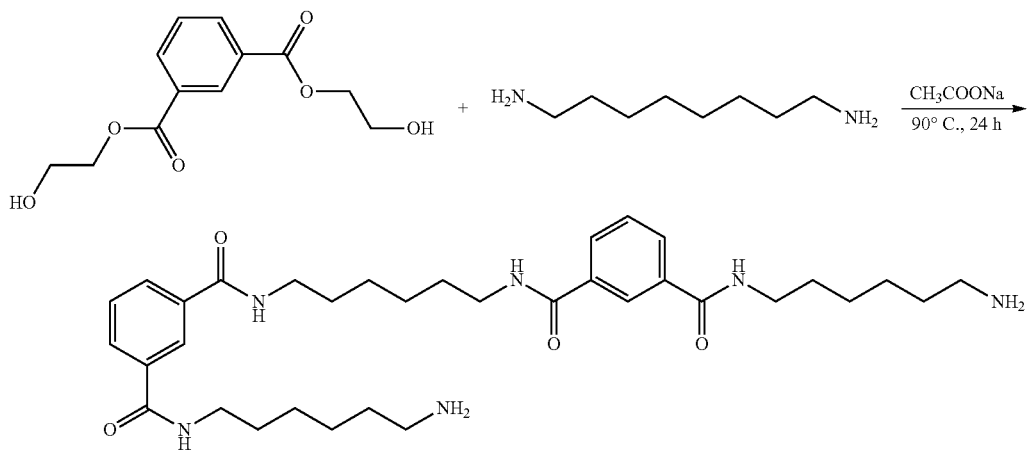

The result of the reaction was then dropwise added to 500 mL of RO water, which was stood for one day to generate white solid. The white solid was collected by centrifugation, washed with RO water, and then put into a vacuum oven at 80° C. for 16 hours to obtain a diamine compound. The diamine compound was dissolved in $D_2SO_4$ to be analyzed by NMR. The NMR spectrum of the diamine compound is listed below: δ8.6069 (aromatic, 6H, d), δ8.3873 (aromatic, 2H, t), δ4.1820 (CH2, 8H, s), δ3.5969 ($CH_2$, 4H, t), δ2.2599 ($CH_2$, 8H, d), δ2.1877 ($CH_2$, 4H, t), δ1.9243 ($CH_2$, 12H, t). As shown in NMR spectrum, the hydrogens of the aromatic ring and the hydrogens of the aliphatic carbon chain have a ratio of 4/18. In the product in Comparative Example 1 (See below), the hydrogens of the aromatic ring and the hydrogens of the aliphatic carbon chain have a ratio of 4/24. As shown in the above comparison, the aromatic ring ratio in Example 1 is higher than that in Comparative Example 1, which proves that the product structure in Example 1 meets the above formula.

Example 2

Synthesis of Diamine Compound 10 g of dimethyl isophthalate (DMI, 0.05 mole), 59.8 g of HMDA (0.5 mole), and 0.7 g of sodium acetate were added to a round bottom bottle (250 mL), and then heated to 90° C. and stirred to react for 24 hours. The result of the reaction was cooled down to room temperature. The reaction is shown below:

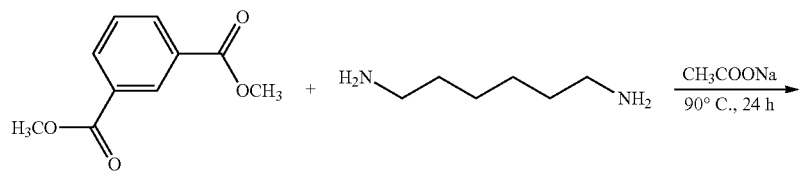

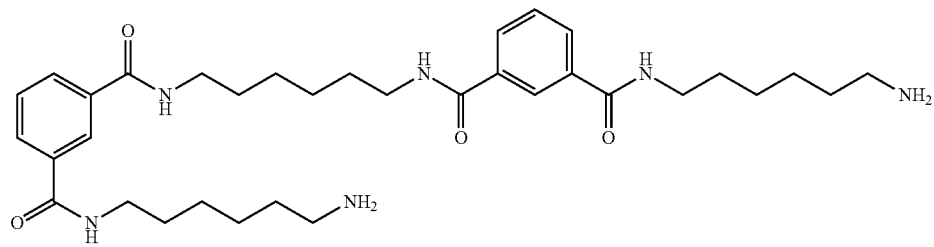

The reaction result was then dropwise added to 500 mL of RO water, which was stood for one day to generate white solid. The white solid was collected by centrifugation, washed with RO water, and then put into a vacuum oven at 80° C. for 16 hours to obtain a diamine compound. The diamine compound was dissolved in $D_2SO_4$ to be analyzed by NMR. The NMR spectrum of the diamine compound is listed below: $\delta 8.7455$ (aromatic, 6H, d), $\delta 8.5074$ (aromatic, 2H, d), $\delta 4.3286$ ($CH_2$, 8H, s), $\delta 3.7047$ ($CH_2$, 4H, s), $\delta 2.4005$ ($CH_2$, 8H, s), $\delta 2.2915$ ($CH_2$, 4H, s), $\delta 2.0677$ ($CH_2$, 12H, d). As known from Examples 1 and 2, different isophthalates could react with the diamine to form the same diamine compound.

Example 3

Synthesis of Diamine-Diacid Salt 1.5 g of the diamine compound prepared by Example 1 (0.0025 mole), 0.65 g of adipic acid (0.0044 mole), and 30 mL of ethanol were added into a round bottom bottle (50 mL), and then heated to 80° C. and stirred to react for 24 hours. The reaction is shown below:

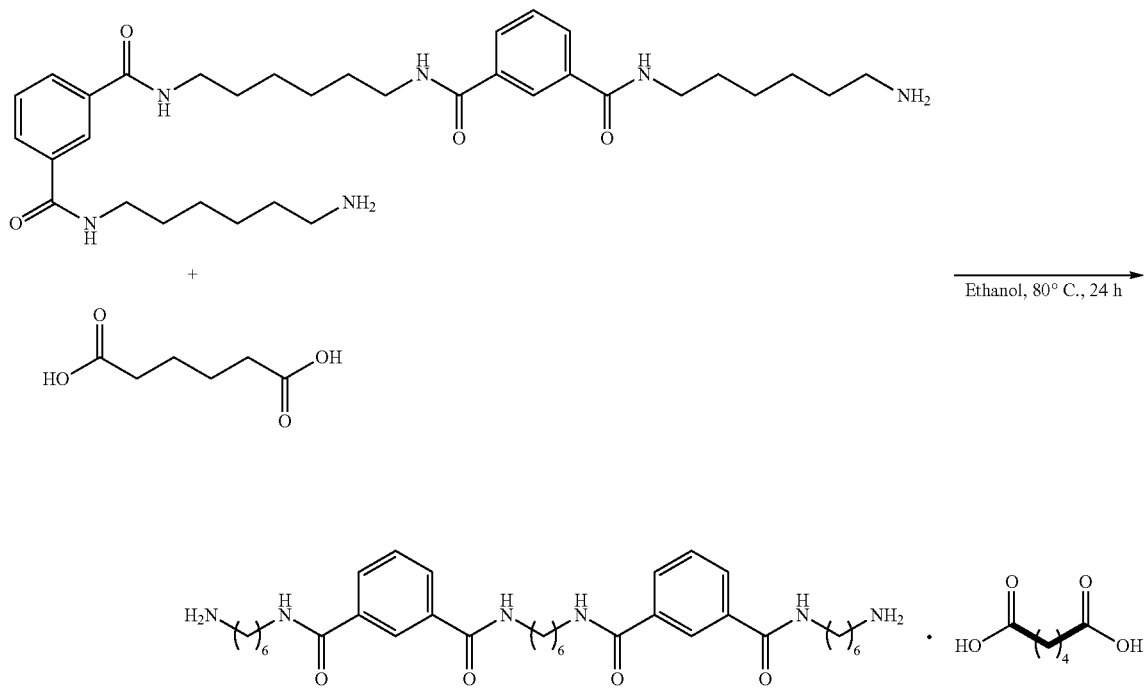

The result of the reaction was cooled down to room temperature to generate solid precipitation, which was collected by centrifugation. The solid was washed with ethanol, and then put into a vacuum oven at 80° C. for 16 hours to obtain a diamine-diacid salt. The diamine-diacid salt was dissolved in $D_2SO_4$ to be analyzed by NMR. The NMR spectrum of the diamine-diacid salt is listed below: $\delta 8.5912$ (aromatic, 6H, t), $\delta 8.3694$ (aromatic, 2H, t), $\delta 4.1671$ ($CH_2$, 8H, s), $\delta 3.5478$ ($CH_2$, 4H, s), $\delta 3.3793$ ($CH_2$, 4H, s), $\delta 2.3126$ ($CH_2$, 4H, s), $\delta 2.2321$ ($CH_2$, 8H, s), $\delta 2.1350$ ($CH_2$, 4H, s), $\delta 1.9068$ ($CH_2$, 4H, s), $\delta 1.8672$ ($CH_2$, 8H, s).

Example 4

Synthesis of Copolymer 1 g of the diamine-diacid salt prepared by Example 3 was added into a round bottom bottle (25 mL), heated to 240° C. and stirred to react for 7 hours. The reaction is shown below:

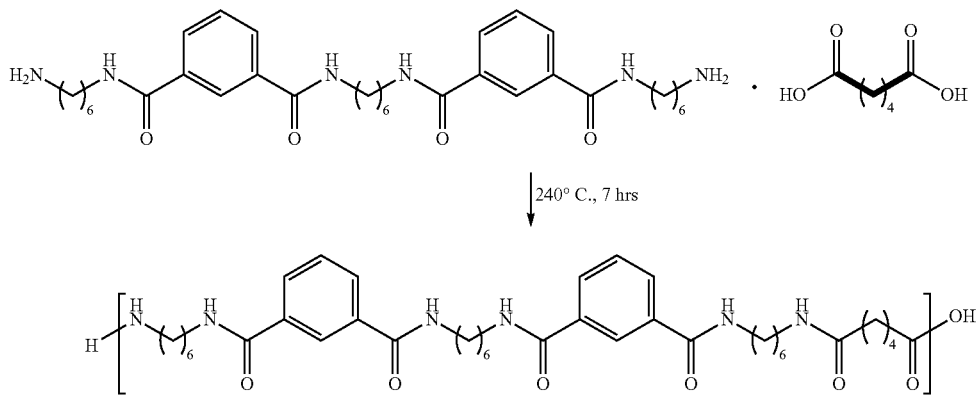

The result of the reaction was sampled at 240° C., and then put in a vacuum oven at 80° C. for 16 hours to obtain a copolymer. The copolymer was dissolved in $D_2SO_4$ to be analyzed by NMR. The NMR spectrum of the copolymer is listed below: δ8.6632 (aromatic, 6H, s), δ8.4371 (aromatic, 2H, s), δ4.2542 ($CH_2$, 8H, s), δ4.0139 ($CH_2$, 4H, s), δ3.2029 ($CH_2$, 4H, s), δ2.3130 ($CH_2$, 12H, s), δ2.1827 ($CH_2$, 4H, s), δ1.9954 ($CH_2$, 4H, s), δ1.9294 ($CH_2$, 8H, s). As shown in NMR spectrum, the copolymer was an alternating copolymer. The copolymer was also analyzed by DSC and XRD. As known from DSC and XRD spectra, the copolymer was in amorphous state. The copolymer had a relative viscosity (Rv) of 2.825 (measured according to the standard ASTM D789, but the solvent, which is formic acid in the standard, was replaced with concentrated sulfuric acid). In addition, the NMR spectrum shows that the I content (e.g. the isophthalate ratio) of the copolymer was 33.3%. The copolymer was also analyzed by DSC to measure its Tg and Tm, as shown in Table 1.

Example 5

Synthesis of Diamine-Diacid Salt 1 g of the diamine compound prepared by Example 1 (0.0016 mole), 0.67 g of sebacic acid (0.0032 mole), and 30 mL of ethanol were added into a round bottom bottle (50 mL), and then heated to 80° C. and stirred to react for 24 hours. The solid was not completely dissolved during the reaction. The reaction is shown below:

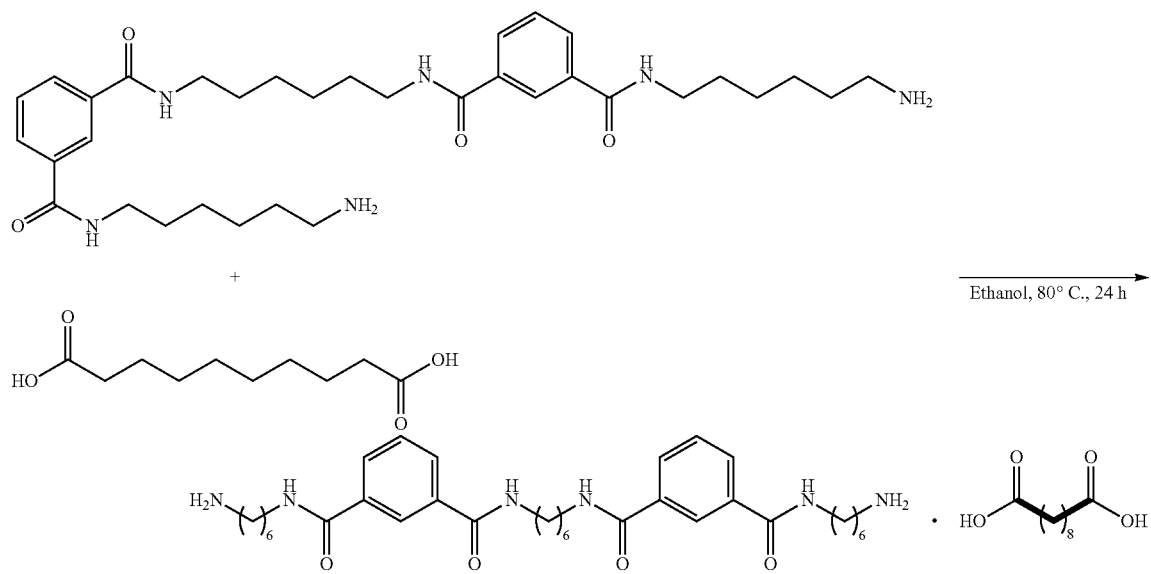

The result of the reaction was cooled down to room temperature to generate solid precipitation, which was collected by centrifugation. The solid was washed with ethanol, and then put into a vacuum oven at 80° C. for 16 hours to obtain a diamine-diacid salt. The diamine-diacid salt was dissolved in $D_2SO_4$ to be analyzed by NMR. The NMR spectrum of the diamine-diacid salt is listed below: δ8.8095 (aromatic, 6H, d), δ8.5901 (aromatic, 2H, t), δ4.3897 ($CH_2$, 8H, s), δ3.7642 ($CH_2$, 4H, s), δ3.5366 ($CH_2$, 4H, t), δ2.4478 ($CH_2$, 12H, d), δ2.3561 ($CH_2$, 4H, s), δ2.1283 ($CH_2$, 4H, s), δ2.0879 ($CH_2$, 8H, s), δ2.0245 ($CH_2$, 4H, s), δ1.9558 ($CH_2$, 4H, s).

Example 6

Synthesis of Copolymer 1 g of the diamine-diacid salt prepared by Example 5 was added into a round bottom bottle (25 mL), heated to 240° C. and stirred to react for 7 hours. The reaction is shown below:

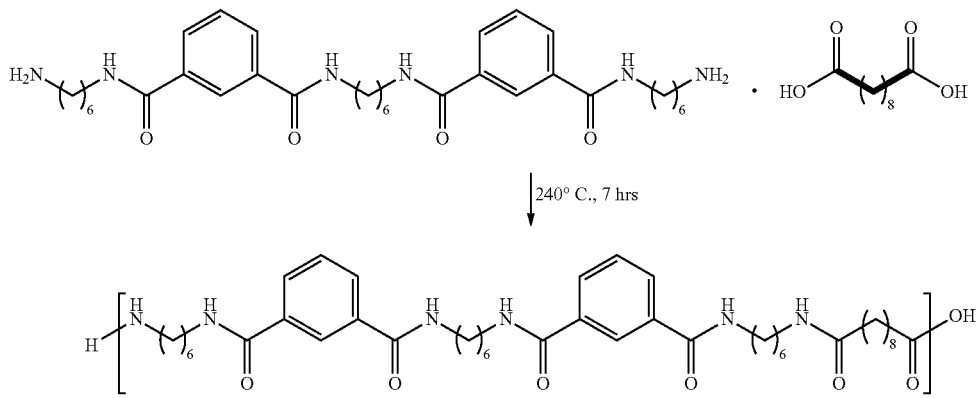

The result of the reaction was sampled at 240° C., and then put in a vacuum oven at 80° C. for 16 hours to obtain a copolymer. The copolymer was dissolved in $D_2SO_4$ to be analyzed by NMR. The NMR spectrum of the copolymer is listed below: δ 8.7637 (aromatic, 6H, s), δ8.5372 (aromatic, 2H, s), δ4.3582 (CH2, 8H, s), δ4.1009 ($CH_2$, 4H, s), δ3.2243 ($CH_2$, 4H, s), δ2.4256 ($CH_2$, 8H, s), δ2.2738 ($CH_2$, 8H, s), δ2.0947~1.9273 ($CH_2$, 20H, m). As shown in NMR spectrum, the copolymer was an alternating copolymer. The copolymer was also analyzed by DSC and XRD. As known from DSC and XRD spectra, the copolymer was amorphous state. The copolymer had a relative viscosity (Rv) of 2.583 (measured according to the standard ASTM D789, but the formic acid of the solvent in the standard was replaced with concentrated sulfuric acid). In addition, the NMR spectrum shows that the I content (e.g. the isophthalate ratio) of the copolymer was 33.3%. The copolymer was also analyzed by DSC to measure its Tg and Tm, as shown in Table 1.

Example 7

Properties of Sheets

The copolymer of Example 4, the copolymer of Example 6, and commercially available copolymers were respectively laminated to sheets (length was 165 mm and the narrowest width was 13 mm) according to the standard ASTM D638. The water absorption analyzed by the standard ASTM D570, the tensile strength was analyzed by the standard ASTM D882-12, the transparency analyzed by the standard ASTM D1746-15, and other properties of the sheets are listed in Table 1.

TABLE 1

| Copolymer type | transparency | Tm (° C.) | Tg (° C.) | Water absorption (%) | Tensile strength (MPa) |
|---|---|---|---|---|---|
| PA-66 | Opaque | 265 | 55-60 | 8.5 | 80 |
| PA-6T | Opaque | 371 | >130 | 5.0 | >200 |
| PA-6I | Transparent | None | >120 | 5.3 | Brittle and difficult to form film |

TABLE 1-continued

| Copolymer type | transparency | Tm (° C.) | Tg (° C.) | Water absorption (%) | Tensile strength (MPa) |
|---|---|---|---|---|---|
| PA-6T/66 | Opaque | 270-330 | 70-130 | 5.7-8.0 (changed by T content) | 120-250 |
| PA-6I/6T/66 | Transparent | None | 65-85 | 6.8-8.0 | 90 |
| PA-6I/6T | Transparent | None | 85-125 | 5.8-6.0 | Brittle and difficult to form film |
| PA-6I/66 | Transparent | None | 85-125 | 5.8-6.0 | Brittle and difficult to form film |
| Product in Example 4 | Transparent | None | About 95-98 | About 5.7 | About 90 |
| Product in Example 6 | Transparent | None | About 85-90 | About 5.1 | About 90 |

PA-66 (commercially available from DSM) had a chemical structure of

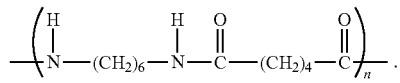

In the above formula, n is the number of repeating units.

PA-6T (commercially available from DSM) had a chemical structure of

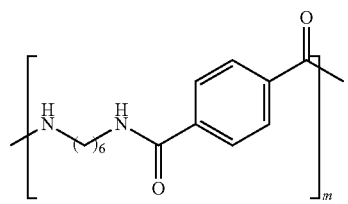

In the above formula, m is the number of repeating units.

PA-6I (commercially available from DSM) had a chemical structure of

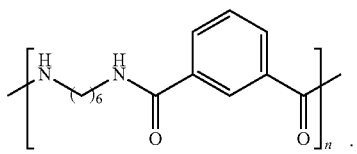

In the above formula, n is the number of repeating units. The I content of the copolymer was 50%.

PA-6T/66 (commercially available from DSM) had a chemical structure of

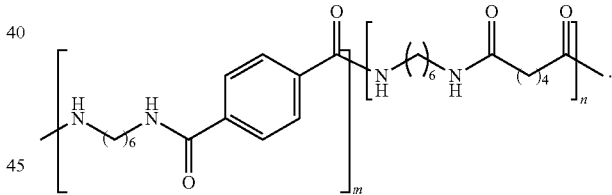

In the above formula, m and n are the numbers of repeating units. PA-6T/66 was a random copolymer.

PA-6I/6T/66 (commercially available from DSM) had a chemical structure of

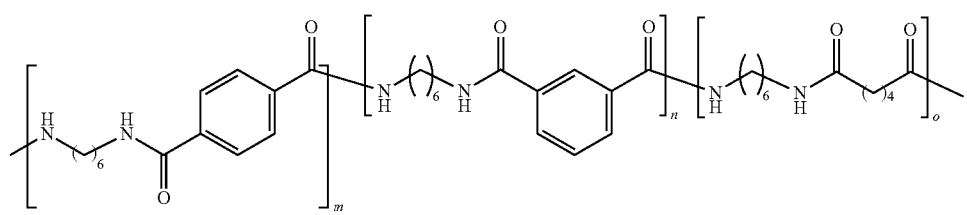

In the above formula, m, n, and o are the numbers of repeating units. The I content of the copolymer (n/(2m+2n+2o)) was less than 20%, and n/m was less than 30%. PA-6I/6T/66 was a random copolymer.

PA-6I/6T (commercially available from DSM) had a chemical structure of

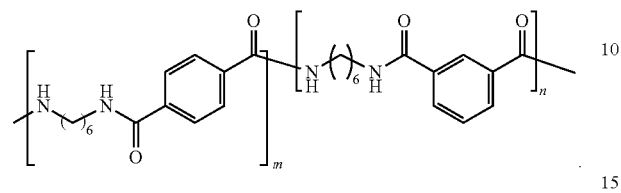

In the above formula, m and n are the numbers of repeating units. The I content of the copolymer (n/(2m+2n)) was less than 25%. If the I content was greater than 25%, it would be difficult to form a film with the copolymer. PA-6I/6T was a random copolymer.

PA-6I/66 (commercially available from DSM) had a chemical structure of

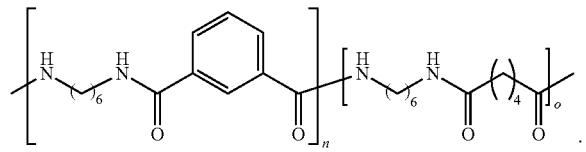

In the above formula, n and o are the numbers of repeating units. The I content of the copolymer (n/(2n+2o)) was less than 25%. If the I content was greater than 25%, it would be difficult to form a film with the copolymer. PA-6I/66 was a random copolymer.

As shown in comparison in Table 1, it was difficult to form a film with the transparent commercially available copolymers, and the commercially available copolymers with film formability were opaque. The copolymers prepared by Examples 4 and 6 had high I content, which could have both transparency and film formability. In addition, the copolymer sheets of Examples 4 and 6 also had low water absorption, high Tg, high tensile strength, and the like.

Comparative Example 1

Synthesis of Diamine Compound 15.2 g of bis(hydroxyethyl)terephthalate (BHET, 0.06 mole), 70 g of HMDA (0.6 mole), and 0.85 g of sodium acetate were added to a round bottom bottle (250 mL), and then heated to 90° C. and stirred to react for 24 hours. White solid was precipitated during the reaction. The reaction result was cooled to room temperature. The reaction is shown below:

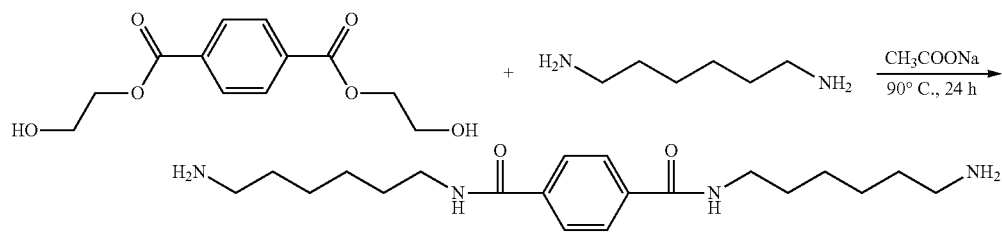

The result of the reaction was then filtered to collect solid. The solid was washed with RO water and then put in a vacuum oven at 80° C. for 16 hours to obtain a diamine compound. The diamine compound was dissolved in $D_2SO_4$ to be analyzed by NMR. The NMR spectrum of the diamine compound is listed below: δ8.4738 (aromatic, 4H, s), δ4.2105 ($CH_2$, 4H, s), δ3.5916 ($CH_2$, 4H, s), δ2.2761 ($CH_2$, 4H, s), δ2.1799 ($CH_2$, 4H, s), δ1.9058 ($CH_2$, 8H, s).

Comparative Example 2

Synthesis of Diamine-Diacid Salt 1 g of the diamine compound prepared by Comparative Example 1 (0.0028 mole), 0.82 g of adipic acid (0.0056 mole), and 30 mL of ethanol were added into a round bottom bottle (50 mL), and then heated to 80° C. and stirred to react for 24 hours. The solid was not completely dissolved during the reaction. The reaction is shown below:

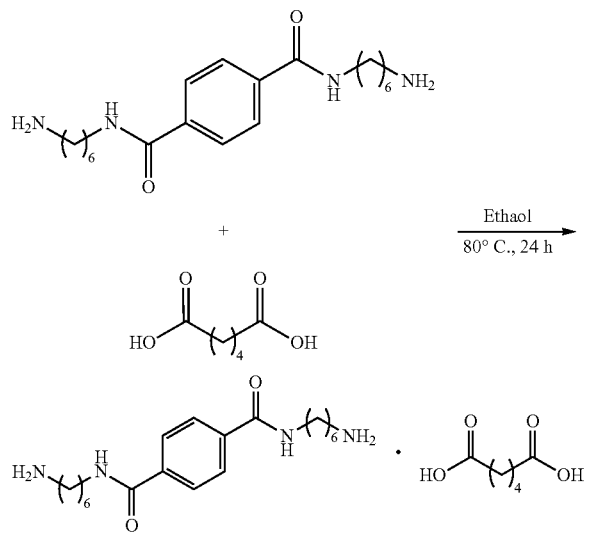

The result of the reaction was cooled down to room temperature to generate solid precipitation, and then filtered to collect the solid. The solid was washed with ethanol, and then put in a vacuum oven at 80° C. for 16 hours to obtain a diamine-diacid salt. The diamine-diacid salt was dissolved in $D_2SO_4$ to be analyzed by NMR. The NMR spectrum of the diamine-diacid salt is listed below: δ8.4706 (aromatic, 4H, s), δ4.2230 ($CH_2$, 4H, t), δ3.6203~3.5691 ($CH_2$, 4H, m), δ3.4230 ($CH_2$, 4H, s), δ2.3563 ($CH_2$, 4H, s), δ2.2727 ($CH_2$, 4H, d), δ2.1941 ($CH_2$, 4H, t), δ1.9046 ($CH_2$, 8H, s).

Comparative Example 3

Synthesis of Copolymer 1 g of the diamine-diacid salt prepared by Comparative Example 2 was added into a round bottom bottle (25 mL), and heated to 290° C. and stirred for 4 hours. The above reaction is shown below:

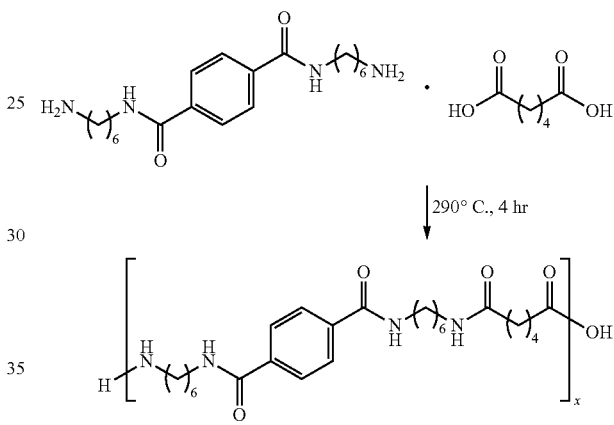

The result of the reaction was sampled at 290° C., and then put in a vacuum oven at 80° C. for 16 hours to obtain a copolymer. The copolymer was dissolved in $D_2SO_4$ to be analyzed by NMR. The NMR spectrum of the copolymer is listed below: δ8.4863 (aromatic, 4H, s), δ4.2682 ($CH_2$, 4H, d), δ3.9897 ($CH_2$, 4H, s), δ3.1734 ($CH_2$, 4H, s), δ2.2781 ($CH_2$, 8H, d), δ2.1541 ($CH_2$, 4H, d), δ1.9681 ($CH_2$, 8H, d). The copolymer was also analyzed by DSC and XRD. As known from the DSC and XRD spectra, the copolymer was crystalline state. The copolymer had a relative viscosity (Rv) of 3.195 (measured according to the standard ASTM D789, but the formic acid used in the solvent in the standard was replaced with concentrated sulfuric acid). In addition, the NMR spectrum shows that the benzene-containing monomer ratio (e.g. the terephthalate ratio) of the copolymer was 25%. The copolymer was also analyzed by DSC to measure its Tg and Tm, as shown in Table 2.

Comparative Example 4

Properties of Sheets

The copolymer of Example 4, the copolymer of Comparative Example 3, and commercially available copolymer PA 66/6I were respectively laminated to sheets (length was 165 mm, and the narrowest width was 13 mm) according to the standard ASTM D638. The transparency analyzed by the standard ASTM D1746-15, the film formability, and other properties of the sheets are listed in Table 2.

TABLE 2

| Copolymer | Example 4 | Comparative Example 3 | PA 66/6I |
|---|---|---|---|
| Monomer type | 2 (Alternating copolymer) | 2 (Alternating copolymer) | 3 (Random copolymer) |
| Transparent or not | Yes (Amorphous) | No (M.P. = 293.16° C.) | Yes |
| Benzene-containing monomer ratio (mol %) | 33.3 | 25 | <25 |
| Tg (° C.) | 98.64 | No Tg between 30~320° C. | 85 |
| Film formability | Film formability and transparent | Film formability but opaque | Film formability and transparent for blend |

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A diamine-diacid salt, having a chemical structure of

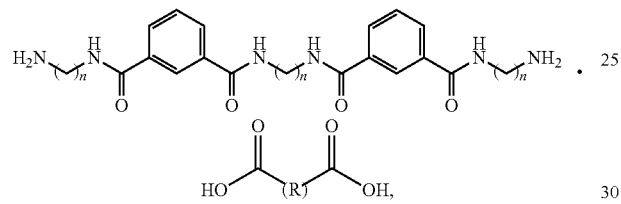

wherein n=6,
R is

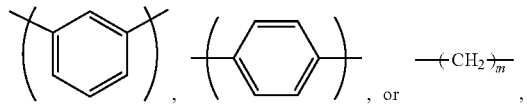

and m=4-8.

2. A method of forming a copolymer, comprising:
(i) mixing a diamine and a diester to form a mixture, and heating the mixture to form a diamine compound, wherein the diamine compound has a chemical structure of

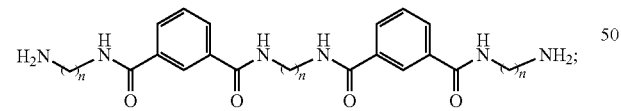

(ii) mixing the diamine compound and a diacid to form a diamine-diacid salt, wherein the diamine-diacid salt has a chemical structure of

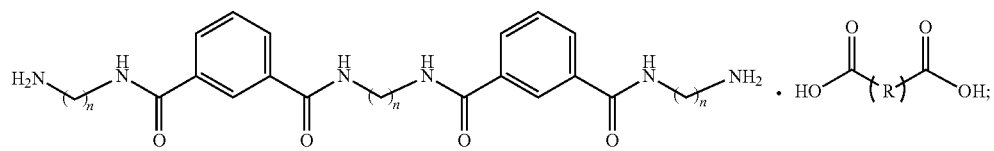

and (iii) heating the diamine-diacid salt to polymerize the diamine-diacid salt for forming a copolymer, wherein the copolymer has a repeating unit with a chemical structure of

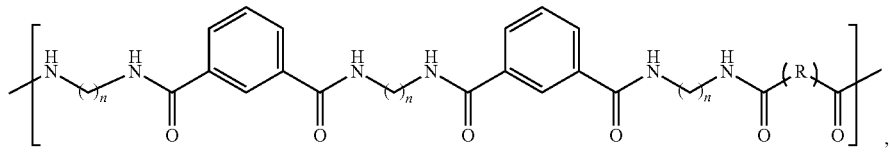

wherein n=6, R is

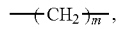

and m=4-8.

3. The method as claimed in claim 2, wherein the step of heating the mixture is performed at a temperature of 70° C. to 100° C., the step of mixing the diamine compound and a diacid to form a diamine-diacid salt is performed at a temperature of room temperature to 80° C., and the step of heating the diamine-diacid salt is performed at a temperature of 200° C. to 260° C.

4. The method as claimed in claim 2, wherein the diamine and the diester have a molar ratio of 6:1 to 11:1, and the diamine compound and the diacid have a molar ratio of 1:1.6 to 1:3.0.

5. The method as claimed in claim 2, wherein the diester comprises bis(hydroxyethyl)isophthalate or dimethyl isophthalate, the diamine comprises hexamethylenediamine, and the diacid comprises adipic acid, or sebacic acid.

* * * * *